(12) United States Patent
Steinberg

(10) Patent No.: US 9,901,487 B2
(45) Date of Patent: Feb. 27, 2018

(54) ANUS CREVICE INSERT

(76) Inventor: C. Howard Steinberg, Monsey, NY (US)

( * ) Notice: Subject to any disclaimer, the term of this patent is extended or adjusted under 35 U.S.C. 154(b) by 629 days.

(21) Appl. No.: 12/721,025

(22) Filed: Mar. 10, 2010

(65) Prior Publication Data

US 2011/0220128 A1    Sep. 15, 2011

(51) Int. Cl.
| | | |
|---|---|---|
| A61B 17/00 | (2006.01) | |
| A61F 13/20 | (2006.01) | |
| A61F 13/00 | (2006.01) | |
| A61F 13/15 | (2006.01) | |

(52) U.S. Cl.
CPC ........ *A61F 13/2011* (2013.01); *A61F 13/204* (2013.01); *A61F 2013/00272* (2013.01); *A61F 2013/00387* (2013.01); *A61F 2013/00825* (2013.01); *A61F 2013/1513* (2013.01); *A61F 2013/15097* (2013.01)

(58) Field of Classification Search
CPC .... A61F 13/02; A61F 13/023; A61F 13/2011; A61F 13/204; A61F 15/008; A61F 2013/00825; A61F 2013/1513
USPC .......... 128/887, 834, 842, 864, 835; 600/32; 604/900, 304, 307, 308, 337, 338
See application file for complete search history.

(56) References Cited

U.S. PATENT DOCUMENTS

| | | | | |
|---|---|---|---|---|
| 4,365,631 | A | * | 12/1982 | Kline ............................ 604/514 |
| 4,445,898 | A | * | 5/1984 | Jensen .......................... 604/337 |
| 5,062,840 | A | | 11/1991 | Holt et al. |
| 6,120,485 | A | | 9/2000 | Gustafsson et al. |
| 6,197,010 | B1 | * | 3/2001 | Leise et al. .................... 604/338 |
| 6,293,930 | B1 | * | 9/2001 | Brunsgaard et al. .......... 604/322 |
| 6,576,429 | B1 | * | 6/2003 | Hallgren ........................ 435/7.1 |
| 7,179,247 | B2 | * | 2/2007 | Mizutani et al. ...... 604/385.101 |
| 2003/0004477 | A1 | * | 1/2003 | Nielsen et al. ............... 604/336 |

(Continued)

FOREIGN PATENT DOCUMENTS

| | | | |
|---|---|---|---|
| DK | 2007 01152 | * | 8/2007 |
| EP | 1 136 048 | | 9/2001 |

(Continued)

OTHER PUBLICATIONS

International Search Report and Written Opinion of the International Searching Authority dated Feb. 8, 2012, from corresponding International Application No. PCT/US2011/020336.

*Primary Examiner* — Ophelia A Hawthorne
*Assistant Examiner* — Caitlin Carreiro
(74) *Attorney, Agent, or Firm* — Buchanan Ingersoll & Rooney PC (57) ABSTRACT

A protective device for insertion into the crevice adjacent to the anus, and cover adjacent portions of the derriere. The protective device cover includes a solid sheet of material with an adhesive on one side which can be used to apply the cover directly onto the portion directly around and adjacent to the anus after it has been inserted into the crevice. The cover also includes slits or holes through which evacuated material may pass through. The cover may also be made from a "plastic-wrap" type material that adheres to human skin when pressure is applied. In an alternate embodiment, a wiping pad is provided between two layers of the cover, which traverses the hole opening when a string is pulled to effect at least partial cleaning in the anus area. This almost eliminates the need for toilet paper, keeps the body clean, and avoids excessive contamination.

10 Claims, 9 Drawing Sheets

(56) References Cited

U.S. PATENT DOCUMENTS

| | | | |
|---|---|---|---|
| 2003/0204174 A1* | 10/2003 | Cisko, Jr. | A61F 5/443 604/338 |
| 2004/0087919 A1 | 5/2004 | Tanaka et al. | |
| 2007/0283962 A1* | 12/2007 | Doshi et al. | 128/206.15 |
| 2008/0262462 A1 | 10/2008 | Bar-Or et al. | |

FOREIGN PATENT DOCUMENTS

| | | | |
|---|---|---|---|
| EP | 1136048 A1 * | 9/2001 | |
| EP | 1 570 731 | 9/2005 | |
| WO | WO 2007134612 A1 * | 11/2007 | A61F 5/443 |

* cited by examiner

FIG. 10B

ANUS CREVICE INSERT

TECHNICAL FIELD

The present invention relates to protective covers adapted to be removably inserted into areas adjacent vacating orifice areas of a body, such as the anus and/or groin area.

BACKGROUND INFORMATION

During the course of fecal elimination, oftentimes the peripheral recessed area or crevice adjacent the anus becomes soiled as the fecal material is eliminated. In such a case, cleansing of the peripheral area around the anus becomes difficult. Additionally, a large amount of toilet paper and other cleansing substances must be used. It often causes a distasteful messy situation to the individual. It is further complicated when the individual has handicaps and it is difficult for him to clean himself. Also, the cost of the cleansing material is considerable and such use of large amounts of toilet paper and the like, is harmful to the environment.

In the areas of sanitary napkins and absorbable pants/diapers, certain designs provide for pad-type surfaces that contain openings in the surface for retaining matter discharged from a human body. Examples include U.S. Pat. No. 7,179,247, titled "Absorbable Article With Protruding Body Fluid Inflow Hole Having an Elastic Side Wall," U.S. Pat. No. 6,120,485, titled "Absorbent Pants Product," and U.S. Pat. No. 5,062,840, titled "Disposable Diapers," each of which are incorporated by reference in their entirety herein.

While the aforementioned designs are suitable for sanitary napkin and absorbable pants/diaper applications, there is a need for a protector that is simple to apply and use during evacuation, which directly is inserted into the crevice immediately surrounding the anus, or other such orifice, and protects the crevice and the surrounding areas.

SUMMARY

The present disclosure relates to a suitable cover capable of being inserted into the crevice containing the anus, and protecting the portions of the derriere immediately surrounding the anus, which cover can be easily applied, easily removed and is disposable.

In one embodiment, the cover can be a solid sheet of material with an adhesive on one side which adhesive can be used to insert the cover directly into the crevice and adjacent the anus and protect the surrounding derriere portion. Specifically, it would adhere to the skin directly surrounding the anus to protect almost all parts from being soiled. The type of adhesive used can be any of the types similar to those applied to band aids, and other topical items that are applied to a person's skin. The sheet may also be perforated to minimize surface contact with the skin to avoid discomfort during removal.

In other embodiments, the cover has a unique shape to effect a more easy removal of the cover from the human body. In further embodiments, the cover is made from a "plastic wrap" type material that physically attaches to skin without the use of adhesives, where a hole in the cover has an adjustment pad attached over the top. In a preferred embodiment, the pad allows a user to adjust the cover over the anal area and peel away the pad just before use. The cover can already be perforated in this area of the anus to permit the cover to be appropriately shaped to enter into the crevice surrounding the anus. Alternately, the cover can be solid permitting the user to form the perforation for the anus and shape the material to fit snugly into the crevice adjacent the anus and then extend onto the derriere. For this purpose, the center of the cover may be thinner than the rest of the cover to permit easy perforation to form the hole in the center. Also, an adapted may be provided to facilitate placement of the protector.

Other objects, features, and advantages according to the present invention will become apparent from the following detailed description of certain advantageous embodiments when read in conjunction with the accompanying drawings in which the same components are identified by the same reference numerals.

BRIEF DESCRIPTION OF THE DRAWINGS

FIG. 9 shows a perspective view of an adapter for use with the present invention; and.

DETAILED DESCRIPTION

Figure 1:
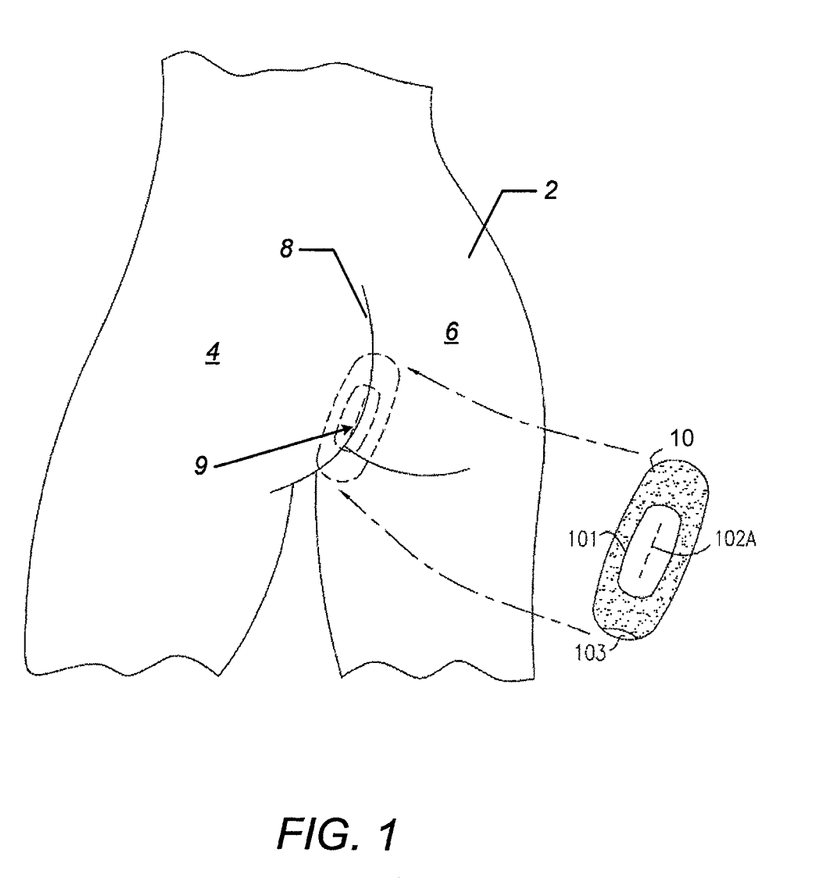
FIG. 1 is a perspective view showing the human derriere and the placement of the present invention.

Referring now to FIG. 1, there is shown a general view of the derriere 2, showing the left portion 4 and right portion 6 with the crevice 8 which is formed between the two sections of the derriere. Along the crevice is located the anus 9 from which typical fecal elimination is emitted. During normal use, the sidewalls of the crevice adjacent to the anus become soiled and in many instances, the soiling even extends beyond the crevice sidewalls onto the actual derriere portion. As a result, large amounts of toilet paper are often needed to cleanse the crevice area, including the sidewalls adjacent to the anus as well as the lateral portions of the derriere itself on either side of the crevice itself.

In addition to large amounts of toilet paper, which must be used, there is often required other cleansing material to protect and remove the soiling. This costs large sums, contaminates the environment and provides a mess and disturbance to the user.

As shown, there is provided a cover 10 which is placed over the anus area. The cover is such that using a finger, applicator, or the like, the center portion is actually inserted within the crevice so that it extends up to and adjacent to the anus without necessarily disturbing the anus or restricting the flow of excrement from the anus. At the same time, it will also serve to cover portions of the derriere adjacent to the crevice to protect those areas as well.

Figure 2:
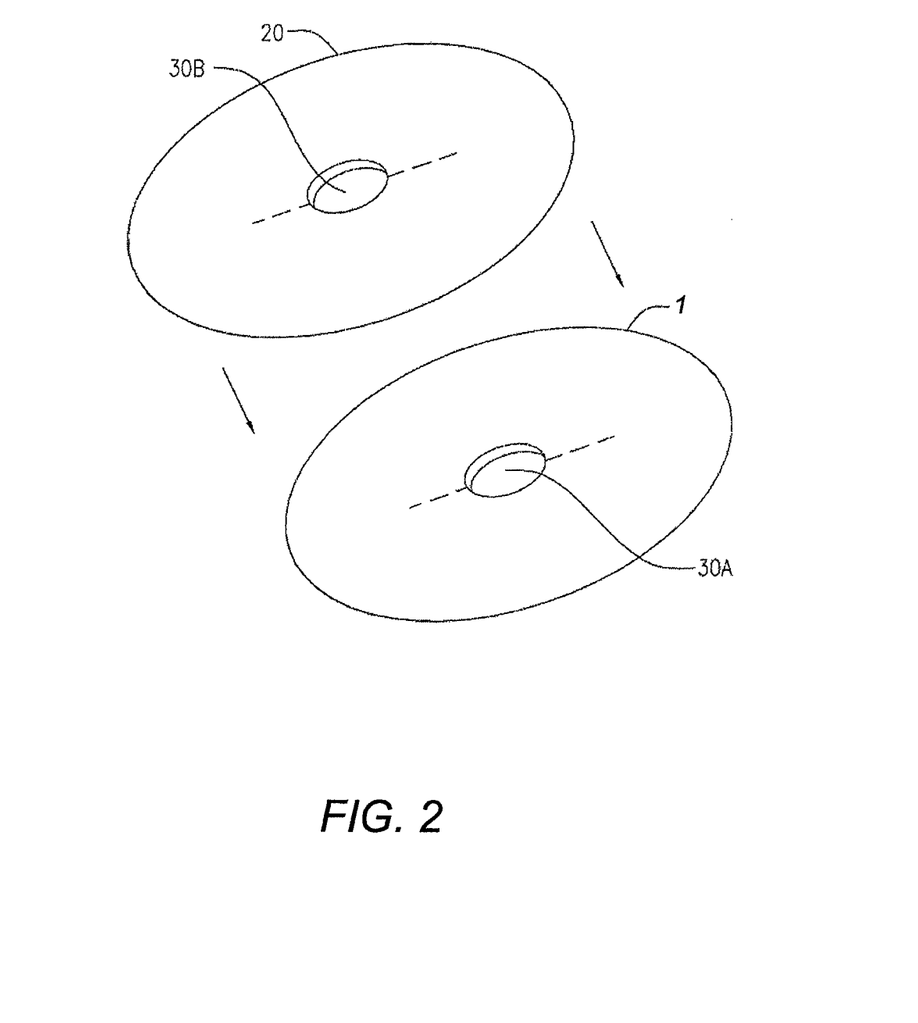
FIG. 2 illustrates a first exemplary embodiment of an anus crevice insert and protector.

In the embodiment illustrated in FIG. 2, the anus insert and protector 1 is a solid sheet of material with an adhesive on one side which adhesive can be used to apply the cover directly onto the derriere portion, and snugly into the crevice adjacent to the anus. The type of adhesive used can be any of the types similar to those applied to band aids, and other topical items that are applied to a person's skin. To protect the adhesive from inadvertently attaching to unwanted items, an adhesive jacket 20 may be overlaid on cover 10 to protect it. Prior to use, adhesive jacket 20 would be removed, and the cover applied so that it is inserted into the crevice and adheres to the skin. Thus, similar to a band-aid that has a protective layer over the adhesive, the jacket 20 can be removed to expose the adhesive on the cover prior to its use. When one is ready to use it, the user will peel off the layer thereby exposing the adhesive for use in inserting the cover into the crevice as well as covering the derriere around the anus.

In a preferred embodiment, cover 100 includes a preformed hole 30A, which would be arranged over the anus, when cover 100 is inserted into the crevice and applied to the human body. The adhesive jacket 20 may have a corresponding hole as well 30B. It should be understood that the cover (and jacket) can also be provided without any opening and once the user inserts it into the crevice and applies it to the derriere, he himself can make an appropriate cut, slit, or simple hole corresponding to the position of the anus. This can be made either with an applied tool or a simple finger. Alternately, the covers can be provided with a pre-formed slit or hole (see FIGS. 3A-F). Furthermore, the size of the opening, whether it be a slit or a circular hole or other shape, can be made of various sizes namely small, medium or large. Of course, the user can begin with the small size, and he could accommodate himself by enlarging the size of the opening.

With the cover placed in the crevice and attached to the derriere, the cover can be shaped so that it adheres to the immediate walls adjacent the anus, as close as possible to the actual exit hole. Thus, when eliminating, there will be almost no soiling of the skin and little, if any, toilet paper needed.

The adhesive can be placed over the entire surface of the cover material or it can be placed only on selected parts of the material. By way of example, just enough so that it will adhere to the immediate peripheral area around the anus. Furthermore, the size of the cover itself can be made in various sizes, either to cover a larger extent area or simply a small peripheral area along the crevice adjacent the anus itself.

The insert and cover can be made of well known material such as paper, plastic, or any other type which can be usable as material applied onto the skin without causing any irritation. By way of example, the numerous types of material, cloth, plastic, paper or the like from which band aids are made can be suitable used for such derriere covers. Furthermore, if the user will make the hole penetration in the insert and cover, it can be of thinner material adjacent the anus to facilitate making a hole in the cover material. Also, perforation can be already existing in the cover for this purpose.

As the insert and cover is made of soft pliable material, and as the adhesive covers the area around the anus, when a hole is made, the portions of the cover adjacent to the hole will adhere closely to the crevice wall adjacent the anus. Thus, they will actually bend upwardly toward the anus covering the crevice wall adjacent the anus itself. As a result, much of the excrement which normally might contaminate the area around the anus will now only contaminate the cover and will not affect the actual skin area. This will cause less irritation and damage to the skin area itself from the fecal material. Additionally, once the cover is removed and it removes the excrement along with it, there will be very little required to maintain cleanliness of the anus itself. As a result, there will be less irritation due to rubbing in that area. Furthermore, there will be almost no toilet paper required to be used to cleanse the area itself.

Figure 3A:
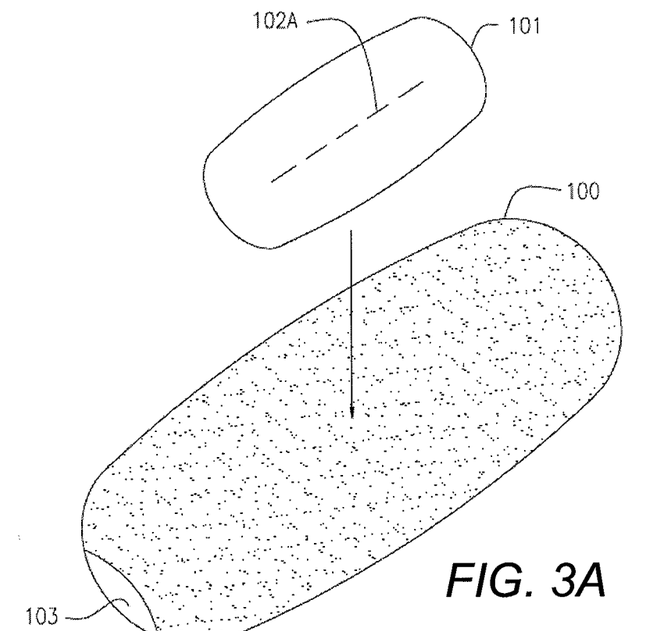
FIGS. 3A-F illustrate other exemplary embodiments of the present invention with a vacating hole of various types and shapes.

FIG. 3A illustrates another exemplary embodiment of an insert and cover for use as an anus protector. The item comprises an exterior layer 100 that is affixed to an interior layer 101. The exterior layer 100 of the cover would be the layer furthest from the body when inserted and applied, and preferably is made from woven fabric, or suitable plastic or latex rubber material which has a biocompatible adhesive or glue. The adhesive chosen is one that will adhere to human skin and yet be easily removed with slight pulling with no adverse effects to the skin. Such adhesives are well known in the art. The adhesive can be placed over the entire surface of the insert and cover material or it can be placed only on selected parts of the material. By way of example, just enough adhesive is applied so that it will adhere to the crevice wall immediately adjacent to the anus. The adhesive for adhering the exterior layer to the human body may be the same adhesive used to affix the exterior and interior layers together. Preferably, the adhesive used to affix the two layers should have stronger adhesive qualities. Under a preferred embodiment, at least one end 103 of the exterior layer 100 is not configured with adhesive, to aid in removing the cover after use. It should be understood that the cover can be made of paper, or any other type of covering which can be usable as material applied onto the skin without causing any irritation.

Interior layer 101 covers exterior layer 100, and is configured to be closest to human skin during application. Since the interior layer 101 would be in contact with the skin, the layer should have minimal to no adhesive qualities. Interior layer 101 is preferably made from a water-impermeable material that is flexible, such as a film made of polyolefin resin. Alternately, the water-impermeable material may be a cellulose derivative such as methyl cellulose, hydroxyethyl cellulose, and carboxymethyl cellulose, water soluble polymer such as polyvinyl alcohol, sodium alginate, sodium poly acrylate, polyacrylic ether, polyvinyl pyrrolidone, and a copolymer of isobutylene and maleic anhydride, or biodegradable polymer such as poly lactic acid, polybutylene succinate, starch, and dextrin. Both interior and exterior layers should be made as thin as possible to allow for ease of application, preferably in the range of 0.5-20 mils thick.

Figure 3B:
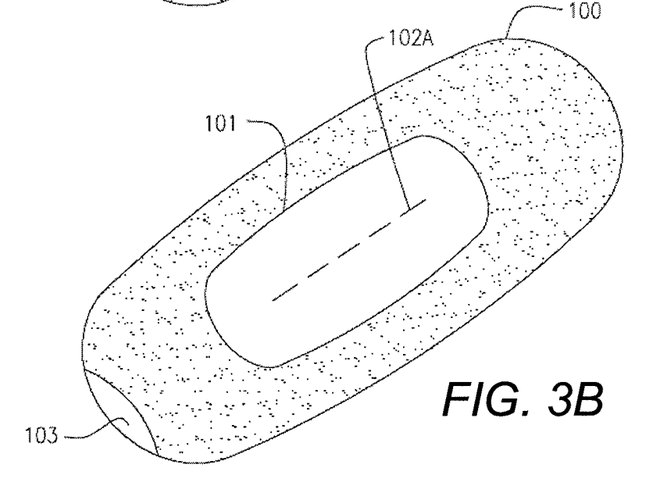
Figure 3C:
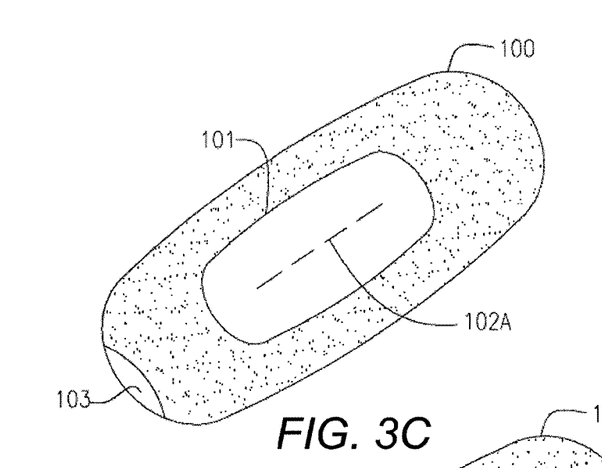
Figure 3D:
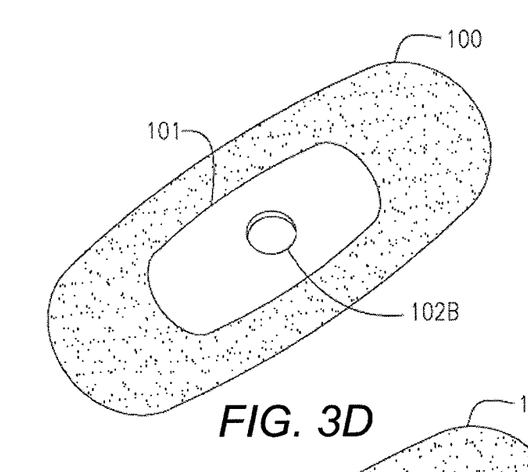
Figure 3E:
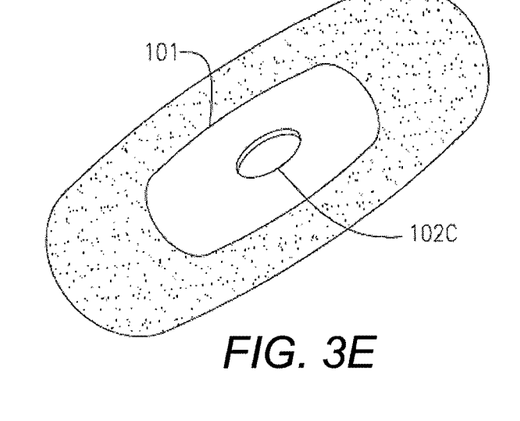
Figure 3F:
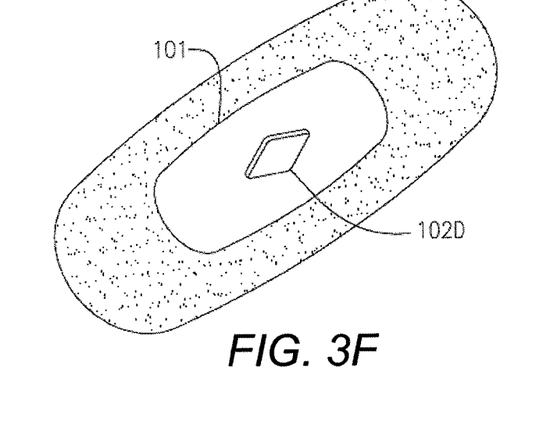

Under one exemplary embodiment, the insert cover can be provided without any opening and once the user inserts it into the crevice and applies it to the derriere, the user can make an appropriate cut, slit, or simple hole corresponding to the position of the anus. This can be made either with an applied tool or a finger. Alternately, the cover can be provided with a pre-formed slit 102A as shown in FIG. 3A. In the embodiment of FIG. 3B, a pre-formed circular hole is provided through which human waste would be evacuated. Furthermore, the size of the opening, whether it be a slit 102a or a circular hole 102b or other shape 102c (e.g., polygon 102d), illustrated in FIGS. 3C-3F, can be made in various sizes namely small, medium or large. Of course, the user can begin with the small size, and he could accommodate himself by enlarging the size of the opening.

Figure 4:
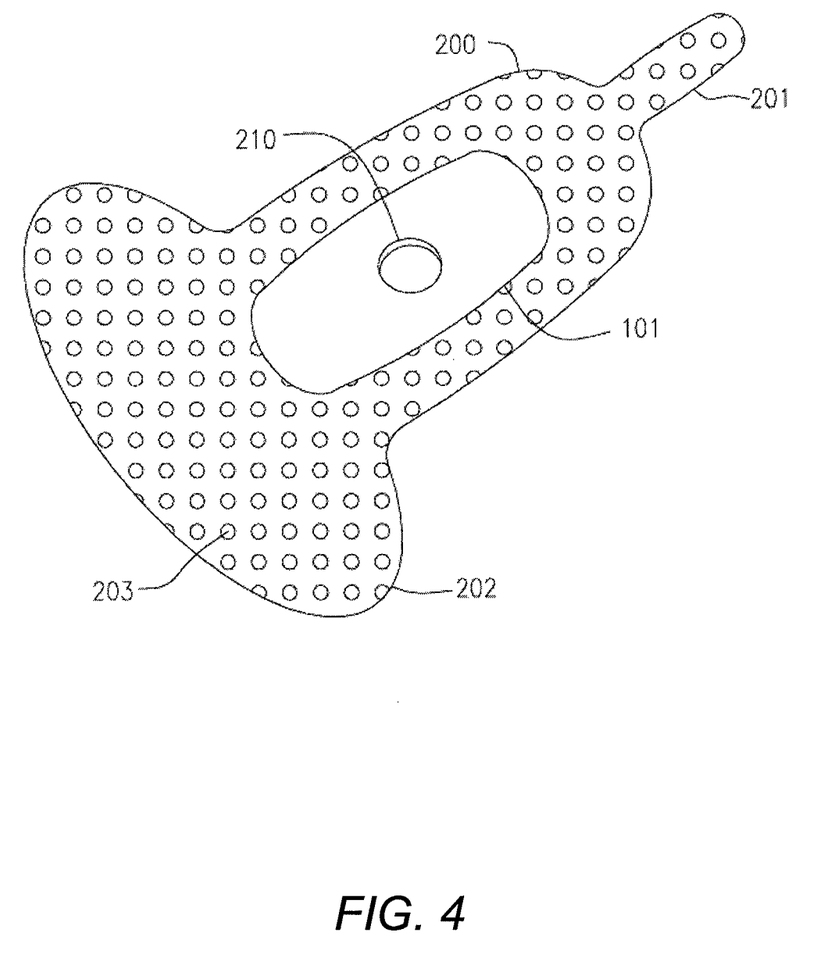
FIG. 4 illustrates another embodiment where the cover has a specialized shape to effect easier insertion and removal of cover from the human body.

FIG. 4 shows an alternate exemplary embodiment of an insert and cover, where exterior surface 200 possesses a specialized shape to form-fit to the human body. Specifically, a front portion 202 of exterior surface 200 could be flared in a lateral direction so that a greater surface area would be available for adhesion to a front part of the body (i.e., pubic region). A back portion 201 of exterior surface 200 is tapered to form a tab-like area, suitable for fitting into the back cleft. Back portion 201 may also contain the same adhesive applied to the remainder of exterior surface 200, or may alternately be adhesive-free. Due to the tabbed shape, back portion 201 provides an easier means for a user to remove the cover after use. The cover also includes an interior portion 201 and hole 210, just as in the embodiments discussed above.

Due to the sensitivity of the anal area, and presence of hair, it is possible to limit the amount of surface area the exterior surface 200 comes in contact with. Accordingly, perforations comprising a plurality of circular holes 203 may be provided. It should be understood that other hole shapes (e.g., squares, diamonds, hexagonal, etc.) would accomplish the same effect.

Figure 5:
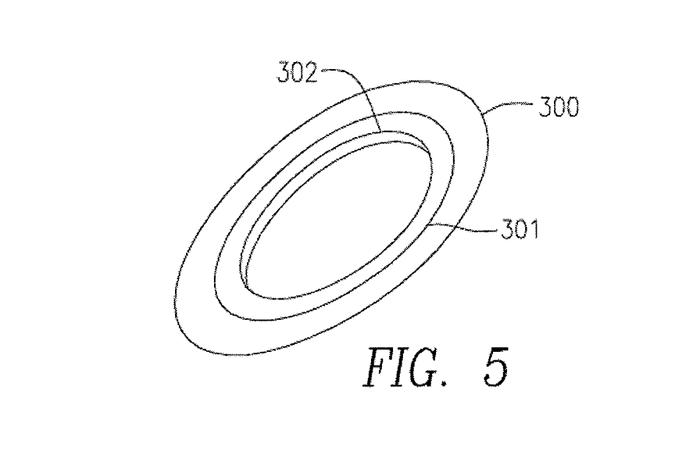
FIG. 5 illustrates another embodiment of the invention.

The size of the insert and cover itself can be made in various sizes, either to cover a larger extent area or simply a small peripheral area around the anus itself. In the exemplary embodiment of FIG. 5, exterior layer 300 is made to insert into the crevice adjacent the anus and to cover only the nearby vicinity of the derriere (i.e., 1½-3 inches), and contains the appropriate adhesive, as discussed above. Interior layer 301 is made from water-impermeable material and surrounds the outer area 302, while leaving a sufficient area exposed on exterior layer 300 to allow adhesion to the skin. Due to the smaller size, interior layer 301 may be made thicker to provide structural support to the surrounding outer area 302, or alternately include an insert (not shown) to support the opening 302.

Figure 6:
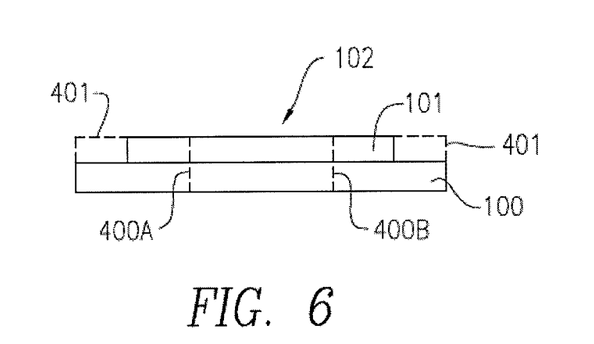
FIG. 6 illustrates a side view of the invention illustrated in FIG. 2A.

FIG. 6 illustrates a side view of the insert and cover for anus protection. Referring partially to the embodiments in FIGS. 3A-F, exterior layer 100 is covered by interior layer 101, and affixed using an adhesive or glue that is water-impermeable. Hole 102 extends through interior layer 101 and exterior layer 100, forming walls 400A and 400B, which serve as a means for allowing evacuated waste to flow through. Under one exemplary embodiment, since exterior layer 401 possesses an adhesive surface, a protective cover or film is placed over exterior layer 401. During normal use, the film would be peeled away by the user before applying to an orifice area.

Figure 7A:
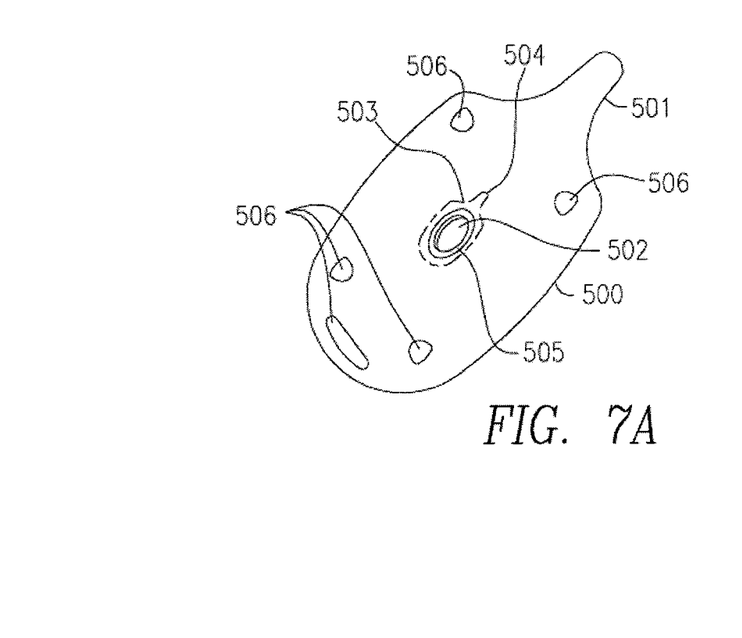
FIG. 7A is yet another illustrative embodiment of the invention.

FIG. 7A illustrates yet another embodiment, where the insert and cover 500 is made from a "plastic wrap" type material, preferably made from a water-impermeable vinyl or polyvinylchloride molecular configuration, which would provide an adhesive "cling" throughout the entire surface. The cover material should also possess a suitable electrical charge to allow for increased adhesion. Plasticizers may be included in the material for the cover 500 to allow it to stretch during application. In an alternate embodiment, the cover 500 may comprise two overlying sheets of cellular tissue on one side and polyethylene on the other side. The polyethylene sheet may be coated with an adhesive, covered with a release tape in the form of a removable cover strip, e.g. glassine paper. Alternately biodegradable materials, such as polystyrene-based stretch film may also be used for cover 500.

The thickness of insert and cover 500 should be very thin (e.g., 0.5-2.0 mils) to allow ease of insertion and adhesion. Because the device is so thin, a hole support 505, preferably made from plastic or rubber, can encircle hole 502 to support and/or maintain the hole opening during use. Similar to the embodiment of FIG. 4, a tab portion 501 is provided at the back of the cover 500, in order to fit in the black cleft when applied. During removal, tab 501 provides an easy means for removal after use. In an alternate embodiment, adhesive areas 506 may be provided in advantageous portions of cover 500 (as shown in the exemplary embodiment of FIG. 7A) to increase adhesive qualities of the cover.

Figure 7B:
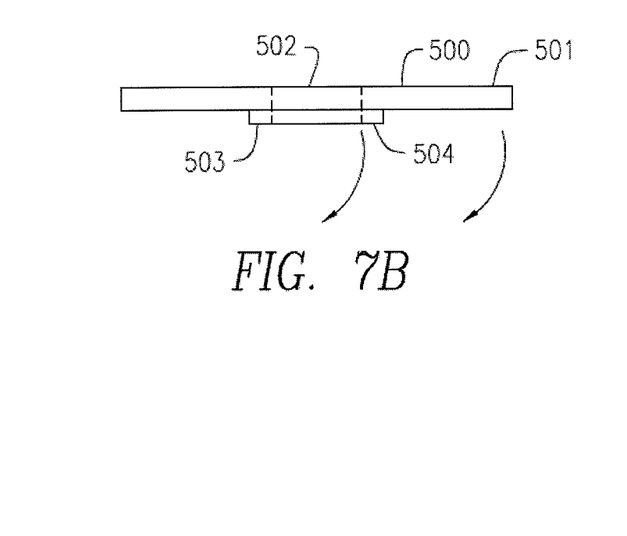
FIG. 7B illustrates a side view of the embodiment shown in FIG. 7A.

In contrast to the embodiments of FIG. 3A-F, the insert and cover 500 is equipped with a removable adjustment pad 503, which covers hole 502 from an exterior surface as show in FIG. 7B. Pad 503 is configured to be larger than hole 502 and is affixed to the surface of cover 500 with adhesive. Similar to insert and cover 500, pad 503 preferably has a tabbed end 504 that allows easy removal of pad 503 from the cover 500 prior to use. Under this configuration, a user can adjust the hole 502 to be over the anus without having to physically touch the area. Once the device is inserted in the crevice adjacent the anus, and placed over the sides of the derriere, the user would remove the tab (see arrow in FIG. 7B) to expose the hole. Subsequently, the user would apply pressure over the remaining surface of the insert and cover 500 to adhere it to the skin.

Figures 8A, 8B:
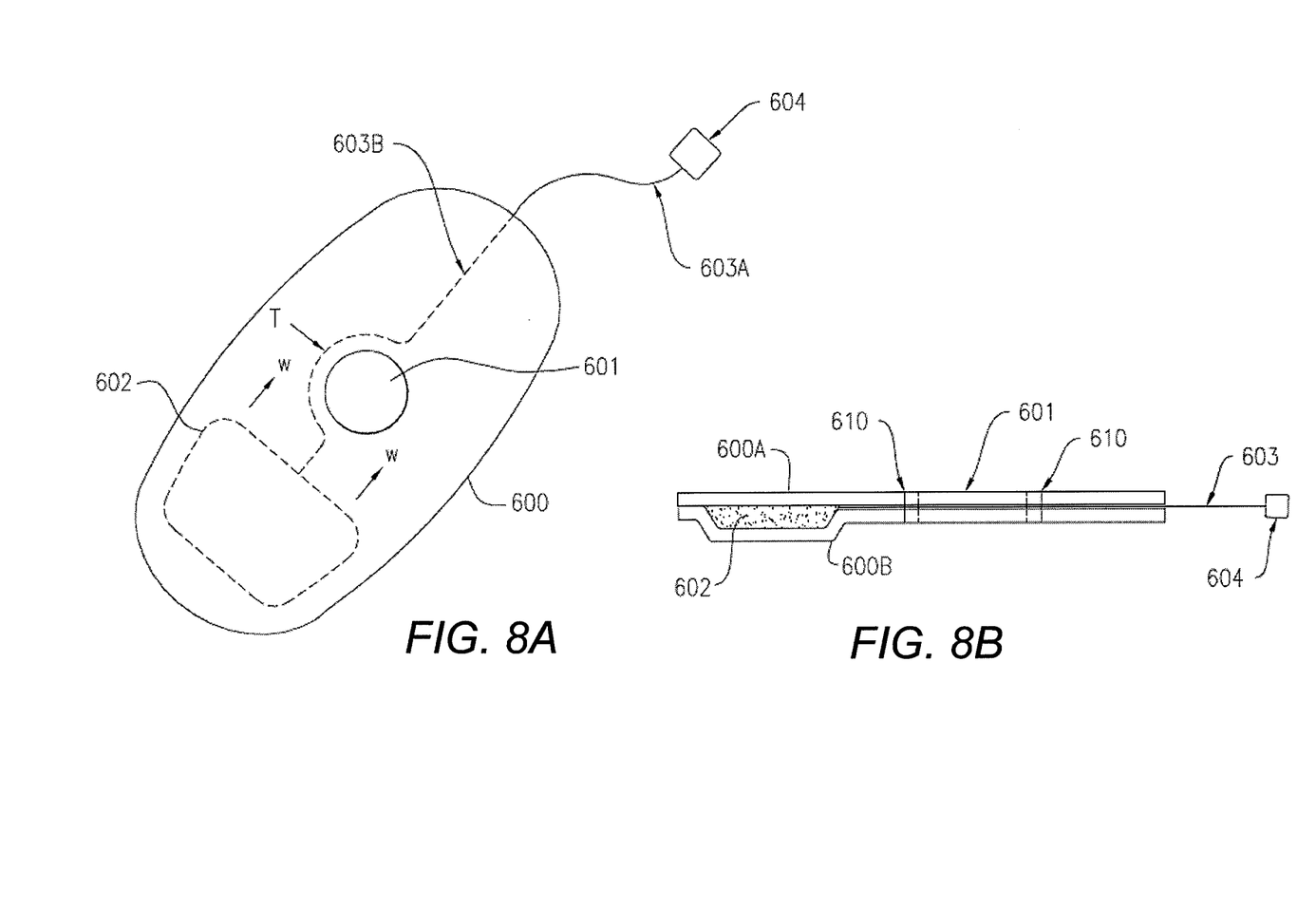
FIG. 8A illustrates yet another embodiment of the invention, which includes a wiping pad.
FIG. 8B illustrates a side view of the embodiment shown in FIG. 8A.

Turning to FIGS. 8A and 8B, another exemplary embodiment is illustrated, where a wiping pad 602 is provided between two layers (600A, 600B) of insert and cover 600. Wiping pad 602 is attached to a string (603B, 603A) that runs continuously through the body of cover 600 and to the outside, where tab 604 is affixed. During use, and after elimination of the feces, a user pulls on tab 604 which creates tension in the string, which ultimately forces wiping pad 602 to move to the rear of cover 600 (see FIG. 8A, "W"), effectively providing at least partial cleaning of the anal area.

To facilitate movement of wiping pad 602, the edge of hole 601 is sealed with a mild adhesive (610) that would break apart when the tension from the string 603 during pulling (FIG. 8B, "T") brings the string through to the center hole 601. After the initial break of the adhesive, the remaining mild adhesive breaks apart when wiping pad 602 is brought forward.

The anus insert and cover described above can be stored in a container and be placed directly in the bathrooms or individual stalls, in which case they can be extracted and used by each user similar to the toilet seat covers. Alternately, they can be folded and prepackaged so that the user can carry one or multiples of these. To the extent that the user carries them, they can be individually folded and packaged for single use or packaged in a bundle and the user extracts them individually from a container that he carries. After use, the entire insert and cover will be flushed or otherwise disposed of in a wastebasket.

To that end, the material used in the insert and cover may also be adapted to conform to various "green" technologies and provide a lessened impact upon the environment. For example, covers may be made from biodegradable polymers such as aliphatic diols, aliphatic-aromatic copolyester, or any organic plastics derived from renewable biomass sources, such as vegetable oil, corn starch, pea starch or microbiota. In this case, materials should generally conform to biodegradability certifications EN 13432, ASTM D6400 and biobased certification ASTM D6866.

While use has been described in connection with fecal elimination, it should be appreciated that such coverings can also be utilized by females during urination to protect the surrounding area from being splashed or otherwise soiled during urination.

In addition to providing the benefit of avoiding soiling by the elimination process, either fecal or urination, it should also be appreciated that this protective insert and cover can also provide medical protection by avoiding contamination with toilet seats, and other material on which the user typically sits. Thus, in many cases, this can serve a similar purpose of a toilet seat cover. While on the one hand it protects the anus from elimination soiling and almost eliminates the use of toilet paper, it also protects the anus and surrounding area from contamination from dirty toilet seats and the like.

To that extent, if the anus covers are large enough, they can replace toilet seat covers and thereby provide both the benefit of the toilet seat cover, as well as the benefit of the derriere cover.

It should be appreciated that instead of a single unitary insert and cover such as a circular section or the like, as we are dealing with the two sides of the anal slit, elongated strips could likewise be used. In that case, a strip would be placed on either side of the anal section and each section inserted in the crevice adjacent each side of the anus. The two individual sections can then serve a similar purpose as a single unitary round or oval section.

Through use of the single strip, the individual need not make an opening but simply applies each of the two strips separately to cover each of the separate sides of the crevice adjacent to the anus. Furthermore, through use of the strip material, it can be placed on a continuous roll of elongated strip section similar to toilet paper. The user can pull off one or more sections and apply it individually on either side of the crevice, respectively, adjacent the anus as needed. This could facilitate making it available for users without having numerous different sizes and shapes.

Various types of medicaments or creams, salves, etc., can also be applied adjacent the opening, if need.

Figure 9:
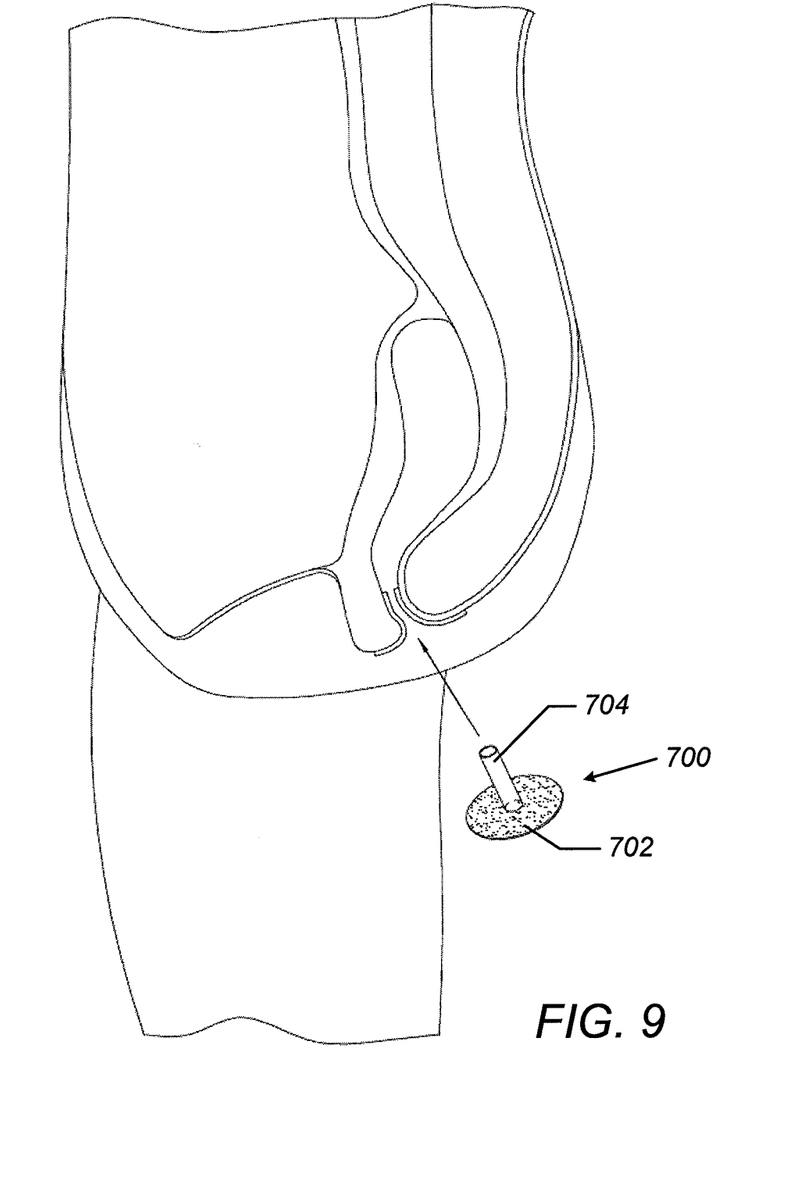
Figure 10A:
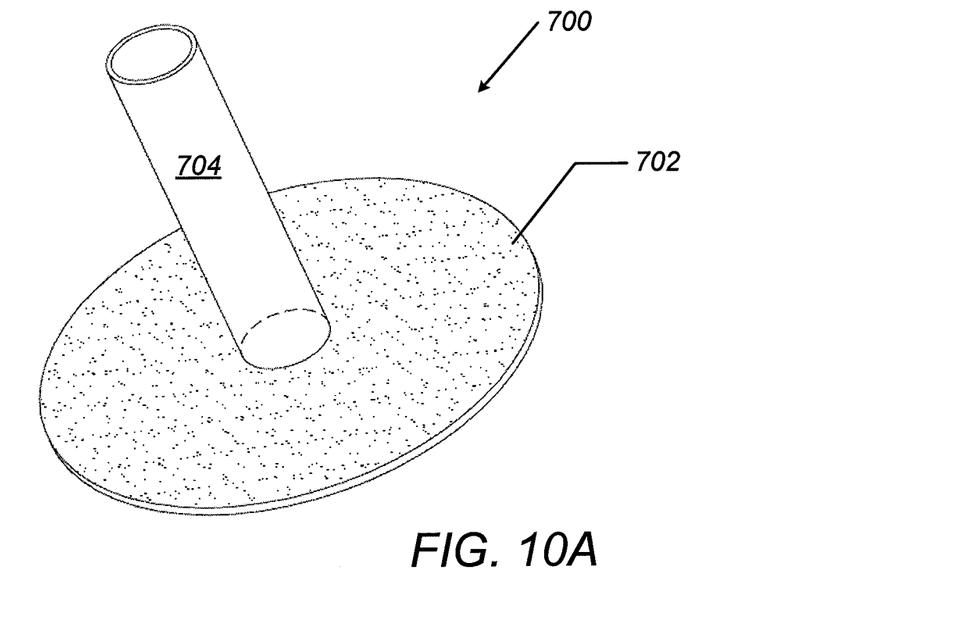
FIGS. 10A & B show the separate parts of the adapter shown in FIG. 8.
Figure 10B:
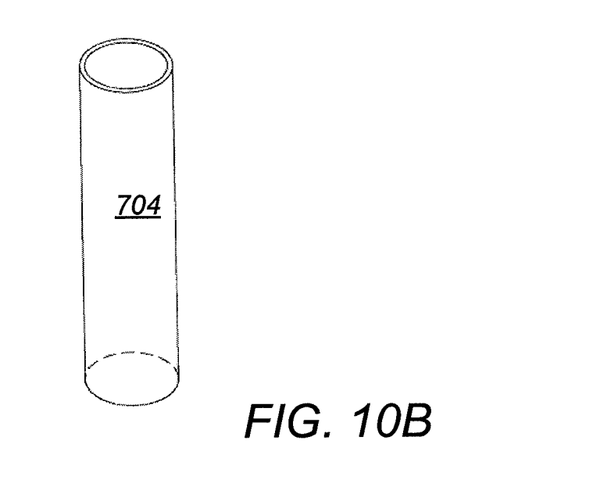

Referring now to FIGS. 9, 10A and 10B, there is shown the use of an applicator 700 for aid in making use of the insert and cover of any of the devices heretofore described. The applicator includes a base portion 702 and a stem portion 704. The applicator can be used in a number of different ways. In one method, the insert and cover of the present invention is first placed on the derriere. The portion of the device is inserted into the crevice adjacent the anus and the derriere is then covered with the rest. After the insert and cover is adhered to the skin, the applicator can then be used to make a center hole corresponding to the anus, avoiding the need for the user to use parts of his own body such as his finger, or the like to make the hole for the anus.

Alternately, the device of the present invention can be loaded onto the base 702 of the applicator with the stem 704 extending into an existing or a created hole on the device. With the device of the present invention placed on the base of the applicator, the applicator is then used to properly guide the device of the present invention and place it on the sides of the crevice adjacent to the anus. Thereafter, the rest of the cover can be adhered to the sides of the derriere and the applicator removed.

As shown in FIG. 10A, the applicator 700 is shown with the base 702 and the stem 704. FIG. 10B shows the presence of the stem 704. In various embodiments the stems can be made removable so that they can be single use stems and therefore, simply inserted into the base and used individually by each individual separately to avoid contamination.

Although the invention has been described with reference to particular arrangements and embodiments, these are not intended to exhaust all possible arrangements or embodiments, and indeed many other modifications and variations will be ascertainable to those of skill in the art. Also, while specific materials are mentioned in this document, one skilled in the art would appreciate that other materials may be used or substituted. This application covers any adaptations or variations of the present invention. Therefore, the present invention is limited only by the claims and all available equivalents.

What is claimed is:

1. A protective device for insertion into a user's crevice adjacent to an anus and covering adjacent portions of a derriere and without any part entering the anus, the device consisting of:
    a flexible flat exterior layer and a smaller flat flexible interior layer, both layers made from a water-impermeable material, the interior layer overlying the exterior layer and forming a center section of the protective device, the portion of the exterior layer not covered forming a peripheral section, the center section capable of being inserted into the crevice adjacent to an anus,
    wherein said flexible exterior layer comprises an adhesive applied to substantially an entire surface of the exterior layer to be able to adhere to the interior layer and to portions of the derriere adjacent the crevice, the water-impermeable material facing the body of the user when the protective device is applied,
    wherein said center section comprises an opening through both layers keeping the anus exposed to the atmosphere thereby permitting excretion from the anus directly into the atmosphere, and without covering the anus and surrounds the anus without entering the anus, the interior layer entering the crevice not containing any adhesive facing the body, wherein with the center section inserted in the crevice and the peripheral section adhered to the derriere only the anus is exposed, and
    a single layer of a removable adhesive jacket over the adhesive.

2. The protective device of claim 1, wherein the opening has a shape consisting of one of a slit, a circle, and a polygon.

3. The protective device of claim 1, wherein the protective device has an elongated shape having two ends, wherein one end is tapered.

4. The protective device of claim 3, wherein another end has a lateral flare.

5. The protective device of claim 1 wherein the flexible exterior layer consisting of a water-impermeable material comprises one of a polyolefin resin film, cellulose derivative, a water soluble polymer and a biodegradable polymer.

6. The protective device of claim 1, wherein the exterior surface has a plurality of perforations made through at least a portion of the exterior surface.

7. A protective device for insertion into a crevice adjacent to an anus and to cover adjacent portions of a derriere, and without any part entering the anus, the device consisting of:
    a flexible flat cover formed of a water-impermeable material and having an exterior layer, and a smaller interior layer overlying the exterior layer and forming a central section, the uncovered portions of the exterior layer forming a peripheral section, the water-impermeable material facing the body, the center section configured to be inserted into the crevice adjacent the anus and the peripheral section extending over the adjacent area of the derriere, wherein the center section has a hole support structure encircling a hole in the center section for leaving the anus exposed to the atmosphere thereby permitting excretion from the anus directly into the atmosphere, and without covering the anus, both layers of the center section of the water-impermeable material entering the crevice adjacent the anus without entering the anus; adhesive material covering substantially the entire surface of the exterior layer to adhere to the interior layer and the derriere adjacent the crevice, the interior layer entering the crevice not having any adhesive facing the body, and a pad removable affixed over the adhesive material on one side of the cover, said pad being configured to cover the hole.

8. The protective device of claim 7, wherein the cover is made from one of (a) a water-impermeable vinyl, (b) polyvinylchloride, and (c) a multi-layered sheet comprising cellular tissue on a first side and polyethylene on a second side.

9. The protective device of claim 7, wherein the cover consisting of a tabbed end that is tapered to fit a rear cleft adjacent to the anus.

10. The protective device of claim 7, wherein the cover has a thickness between 0.5 and 2.0 mils.

\* \* \* \* \*